United States Patent [19]

Fukumoto et al.

[11] Patent Number: 4,912,253

[45] Date of Patent: Mar. 27, 1990

[54] METHOD FOR THE PREPARATION OF AN UNSATURATED ALCOHOL OR ESTER THEREOF

[75] Inventors: Takehiko Fukumoto; Akira Yamamoto, both of Niigata, Japan

[73] Assignee: Shin-Etsu Chemical Co., Ltd., Tokyo, Japan

[21] Appl. No.: 347,399

[22] Filed: May 4, 1989

[30] Foreign Application Priority Data

Jun. 6, 1988 [JP] Japan ................ 63-138742

[51] Int. Cl.$^4$ ................ C07C 29/40; C07C 33/025; C07C 33/20; C07C 67/08
[52] U.S. Cl. ................ 560/261; 560/254; 568/813; 568/874; 568/876; 568/909.5; 568/851; 568/841; 556/470
[58] Field of Search ................ 560/261, 254; 568/909.5, 876, 874, 813

[56] References Cited

U.S. PATENT DOCUMENTS

| | | | |
|---|---|---|---|
| 2,873,275 | 2/1959 | Ramsden | 568/909.5 |
| 2,921,940 | 1/1960 | Ramsden | 568/876 |
| 3,080,324 | 3/1963 | Richards et al. | 568/876 |
| 3,161,689 | 12/1964 | Cooper et al. | 568/876 |
| 3,631,179 | 12/1971 | Urry | 568/909.5 |
| 3,856,867 | 12/1974 | Ramsden | 568/909.5 |
| 3,887,603 | 6/1975 | Rundberg et al. | 568/909.5 |
| 4,061,667 | 12/1977 | Schleppnik | 568/909.5 |
| 4,189,614 | 2/1980 | Samain et al. | 568/909.5 |

FOREIGN PATENT DOCUMENTS

| | | | |
|---|---|---|---|
| 1912405 | 10/1970 | Fed. Rep. of Germany | 568/909.5 |
| 88437 | 6/1984 | Japan | 568/876 |
| 456516 | 2/1977 | U.S.S.R. | 568/876 |

Primary Examiner—J. E. Evans
Attorney, Agent, or Firm—Wyatt, Gerber, Burke and Badie

[57] ABSTRACT

An efficient method is proposed for the synthesis of an unsaturated alcohol of the general formula R—CH=CH(CH$_2$)$_{n+1}$OH, in which R is a hydrogen atom or a monovalent hydrocarbon group having 1 to 10 carbon atoms and the subscript n is an integer in the range from 3 to 10, in which an acetate of the formula R—CH=CHCH$_2$OCOCH$_3$ is subjected to a coupling reaction with a Grignard reagent of the formula X$^1$Mg(CH$_2$)$_n$OMgX$^2$, in which X$^1$ and X$^2$ are each a halogen atom, and then the reaction product is hydrolyzed. When the reaction product of the coupling reaction is reacted with acetic anhydride instead of hydrolysis, the corresponding acetate can readily be obtained. These unsaturated alcohols and acetates form a class of important biologically active compounds or intermediates thereof including sex pheromone compounds of insects.

8 Claims, No Drawings

METHOD FOR THE PREPARATION OF AN UNSATURATED ALCOHOL OR ESTER THEREOF

BACKGROUND OF THE INVENTION

The present invention relates to a method for the preparation of an unsaturated alcohol or, more particularly, to a method for the preparation of an ethylenically unsaturated alcohol useful as an intermediate for the synthetic preparation of various kinds of sex pheromone compounds of insects used for the population control of pests, insecticides, growth regulators of plants and insects and the like.

Various synthetic methods are known in the organic chemistry for the synthesis of unsaturated alcohols, of which the methods utilizing a Grignard reagent sometimes provide an efficient route for the synthesis of the desired compound. For example, a method is known in which a coupling reaction is performed between a Grignard reagent obtained by the reaction of magnesium with an $\omega$-haloalcohol, i.e. halohydrin, having the hydroxy group protected with a protective group such as tetrapyranyl ether and an allyl compound such as allyl halides, allyl acetate, allyl methanesulfonate, allyl p-toluenesulfonate and the like.

The above mentioned coupling reaction of a Grignard reagent is not always quite satisfactory in respect of the low yeld of the desired compound and possible isomerization relative to the ethylenically unsaturated double bond which could be suppressed only by carrying out the reaction at a considerably low temperature at the sacrifice of the reaction velocity. In addition, the Grignard reagent per se is prepared by a troublesome process including the steps of protection of the hydroxy group in the starting $\omega$-haloalcohol and deprotection, i.e. elimination of the protective group.

For example, Henrick in Tetrahedron, volume 33, page 1845 (1979) and Samain in Synthesis, page 388 (1978) disclosed a method for the synthesis of (E,E)-8,10-dodecadien-1-ol which is a sex pheromone compound of codling moths *Laspeyresia pomonella* in the reaction carried out at 0° C. or below and expressed by the following reaction equation in the presence of an acid and $Cu^+$ ions:

$$CH_3CH={}^{(E)}CHCH={}^{(E)}CHCH_2OCOCH_3 + XMg(CH_2)_6O\text{—Py}$$
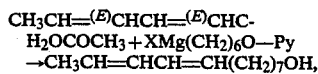
$$\rightarrow CH_3CH{=}CHCH{=}CH(CH_2)_7OH,$$

in which X is a halogen atom and Py is a 2-tetrahydropyranyl group.

Further, Descoin and Samain in Noueau Journal de Chimie, volume 2(3), page 249 (1978) disclosed a method for the synthesis of (E,Z)-7,9-dodecadienyl acetate which is a sex pheromone compound of European grapevine moths by the reaction carried out at −10° C. or at −78° C. and expressed by the following reaction equation in the presence of $Li_2CuCl_4$ followed by hydrolysis and reaction with acetic anhydride:

$$CH_3CH_2CH={}^{(Z)}CHCH={}^{(E)}CHCH_2OCOCH_3 + ClMg(CH_2)_6O\text{—Py}$$
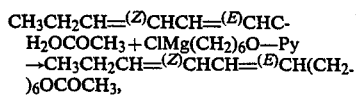
$$\rightarrow CH_3CH_2CH={}^{(Z)}CHCH={}^{(E)}CH(CH_2)_6OCOCH_3,$$

in which Py has the same meaning as defined above.

These synthetic methods are industrially not advantageous because the reaction must be carried out at a low temperature in a special reaction apparatus equipped with a cooling system. In addition, these methods are conducted in a troublesome process involving the steps of protection and deprotection of the hydroxy group. When the protective group of the hydroxy group is an organosilyl group, moreover, the Grignard reagent may sometimes be unstable as is shown by the following equation:

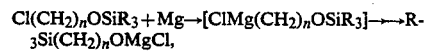
$$Cl(CH_2)_nOSiR_3 + Mg \rightarrow [ClMg(CH_2)_nOSiR_3] \rightarrow R_3Si(CH_2)_nOMgCl,$$

in which R is, for example, a methyl group and n is a positive integer. It is accordingly a conclusion that these prior art methods are not suitable as an industrial process for the mass production of an unsaturated alcohol. Therefore, it is eagerly desired to develop an industrially more advantageous method for the synthesis of unsaturated alcohols.

SUMMARY OF THE INVENTION

The present invention accordingly has an object to provide a novel and industrially advantageous method for the synthesis of an unsaturated alcohol by using a Grignard reagent in a reaction which can be carried out at room temperature without necessitating the troubleome steps of protection and deprotection of the hydroxy groups.

Thus, the method of the present invention for the synthetic preparation of an unsaturated alcohol compound represented by the general formula $$RCH{=}CH(CH_2)_{n+1}OH,$$

in which R is a hydrogen atom or a monovalent hydrocarbon group having 1 to 10 carbon atoms and n is a positive integer in the range from 3 to 10, comprises the steps of:(a) subjecting an acetate of an unsaturated alcohol repre-sented by the general formula

$$R{—}CH{=}CHCH_2OCOCH_3, \quad (I)$$

in which R has the same meaning as defined above, to a coupling reaction with a Grig-nard reagent represented by the general formula $$X^1Mg(CH_2)_nOMgX^2, \quad (II)$$

in which $X^1$ and $X^2$ are each a halogen atom and n has the same meaning as defined above, and then (b) hydrolyzing the thus obtained reaction product.

DETAILED DESCRIPTION OF THE PREFERRED EMBODIMENTS

As is described above, the most characteristic feature in the inventive method consists in the use of the specific Griganrd reagent as the coupling agent represented by the general formula (II) having a $-OMgX^2$ group as the protecting group of the hydroxy group with the acetate of an unsaturated alcohol. Namely, the coupling reaction can be expressed by the following reaction equation:

$$R{—}CH{=}CHCH_2OCOCH_3, + X^1Mg(CH_2)_nOMgX^2 \rightarrow R{—}CH{=}CH(CH_2)_{n+1}OMgX^2 \text{(hydrolysis)}$$
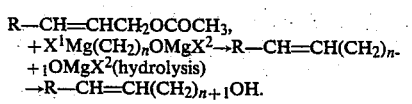
$$\rightarrow R{—}CH{=}CH(CH_2)_{n+1}OH.$$

The Grignard reagent represented by the general formula (II) can be easily prepared by the reaction of metallic magnesium with a conventional inexpensive Grignard reagent such as methyl magnesium chloride with admixture of an ω-haloalcohol of the formula $X^1(CH_2)_nOH$ according to the following reaction equation:

$$X^1CH_2)_nOH + CH_3MgX^2 \rightarrow {}^{X1}(CH_2)_nOMgX^2$$

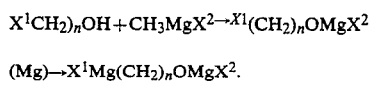

$$(Mg) \rightarrow X^1Mg(CH_2)_nOMgX^2.$$

This Grignard reagent is stable and the nucleophilic activity of the Grignard reagent is not subject to a decrease even with the possibility of tautomerism shown below:

$$X^1Mg(CH_2)_2OMgX^2 \rightleftharpoons {}^{X2}Mg(CH_2)_nOMgX^1.$$

The inventive method is performed merely by reacting the thus prepared Grignard reagent with an acetate of an unsaturated alcohol represented by the general formula (I) given above which is added dropwise to the Grignard mixture in the presence of a copper catalyst followed by hydrolysis of the reaction product so that the troublesome steps of protection of the hydroxy group with a protective group and elimination of the protective group therefrom can be totally omitted. The coupling reaction with the specific Grignard reagent can proceed at a temperature in the range from 10° to 30° C. or at room temperature without the disadvantage of transition or isomerization of the double bond so that no particular cooling system is required for chilling the reaction mixture, for example, to −10° C. or −78° C. as in the prior art methods. This is a great advantage in the industriallization of the process by virtue of saving of the large investment for the cooling facilities.

As an application of this inventive method, (E,E)-8,10-dodecadien-1-ol as a sex pheromone compound of *Laspeyresia pomonella* can be easily synthesized from (E,E)-2,4-hexadienyl acetate by a Grignard coupling reaction in tetrahydrofuran at 20° to 40° C. as catalyzed by Li$_2$CuCl$_4$ in a yield of 60 to 70% according to the following reaction equation:

$$CH_3CH={}^{(E)}CHCH={}^{(E)CH}CH_2OCOCH_3,$$
$$+ClMg(CH_2)_6OMgCl$$
$$(hydrolysis) \rightarrow Ch_3CH={}^{(E)}CHCH=CH^{(E)}(CH_2)_7OH.$$

The Grignard reagent used here has no hydroxy group but the molecular chain end is blocked with a -OMgX$^2$ group which remains intact even after the coupling reaction. In other words, the product molecule by the coupling reaction still has a -OMgX$^2$ group leaving a possibility of further conversion into a functional group of other types by the reaction with a suitable reactant. For example, (E,Z)-7,9-dodecadienyl acetate as the sex pheromone compound of European grapevine moths can be synthesized in a yield of 50 to 60% by the reaction of acetic anhydride with the reaction product of the Grignard coupling reaction according to the following reaction scheme:

$$CH_3CH_2CH={}^{(Z)}CHCH={}^{(E)}CHCH_2OCOCH_3 +$$

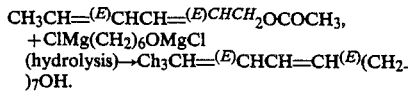

$$ClMg(CH_2)_5OMgCl \longrightarrow$$

$$CH_3CH_2CH={}^{(Z)}CHCH={}^{(E)}CH(CH_2)_6OMgCl;$$
(CuI, in tetrahydrofuran, at 20–30° C.)

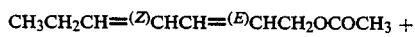

$$CH_3CH_2CH={}^{(Z)}CHCH={}^{(E)}CH(CH_2)_6OMgCl +$$

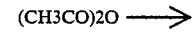

$$(CH3CO)2O \longrightarrow$$

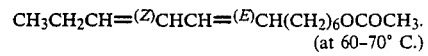

$$CH_3CH_2CH={}^{(Z)}CHCH={}^{(E)}CH(CH_2)_6OCOCH_3.$$
(at 60–70° C.)

The acetate of an unsaturated alcohol or unsaturated-hydrocarbyl acetate used as the starting reactant of the Grignard coupling reaction is expressed by the general formula (I), in which R is a hydrogen atom or a monovalent hydrocarbon group having 1 to 10 carbon atoms, which may be saturated or unsaturated, including linear or branched alkyl groups, alkenyl groups, alkynyl groups and aryl groups. Examples of the acetate compounds include allyl acetate, (E)-2-butenyl acetate, (Z)-2-butenyl acetate, (E)-2-hexenyl acetate, (E)-2-decenyl acetate, (E)-2-dodecenyl acetate, (E)-2,4-pentadienyl acetate, (E,E)-2,4-hexadienyl acetate, (E,Z)-2,4-heptadienyl acetate, (E)-2-hepten-4-yn-1-yl acetate, (E)-2-decen-4-yn-1-yl acetate, 3-phenyl-(E)-2-propenyl acetate, 6-(4'-methylphenyl)-(E)-2-hexenyl acetate and the like.

Both of the E-configuration and Z-configuration are possible as the steric isomerism of the double bond in the general formula (I). It should be noted, however, that the reaction product of the Z-isomer is sometimes subject at least partly to isomerization into the corresponding E-isomer to cause a decrease in the purity relative to the geometrical isomerism.

The other reactant pertaining to the Grignard coupling reaction is a Grignard reagent represented by the general formula (II) given above, in which each of $X^1$ and $X^2$ is a halogen atom independently from the other and the subscript n is an integer in the range from 3 to 10. As is mentioned before, such a Grignard reagent can be prepared from an ω-haloalcohol of the formula $X^1(CH_2)_nOH$ exemplified by 3-chloropropyl alcohol, 5-chloropentyl alcohol, 6-chlorohexyl alcohol, 8-bromooctyl alcohol, 10-bromodecyl alcohol and the like. The Grignard reagent can be prepared by first reacting the ω-haloalcohol with an inexpensive Grignard reagent such as methyl and ethyl magnesium chlorides in a suitable organic solvent, preferably, at 20° to 60° C. to form a magnesium alcoholate and then reacting this magnesium alcoholate with metallic magnesium, preferably, at 60° to 80° C. The organic solvent suitable for the reaction medium is exemplified by tetrahydrofuran, diethyl ether, n-butyl ether, toluene, xylene and the like used either singly or as a mixture of two kinds or more according to need. A preferable solvent is tetrahydrofuran which is used usually in an amount of 400 to 800 g per mole of the starting ω-haloalcohol.

In the next place, a copper catalyst is added to the thus prepared Grignard mixture to which the unsaturated-hydrocarbyl acetate is added to effect the coupling reaction. Suitable copper catalysts include anhydrous halides of monovalent or divalent copper or a complex thereof with a lithium halide. Examples of suitable copper compounds include copper (I) iodide, copper (I) chloride, copper (I) bromide, copper (II) chloride, copper (II) bromide, dilithium tetrachlorocuprate Li$_2$CuCl$_4$ and the like all in an anhydrous state. A preferred copper catalyst in respect of the yield of the product is dilithium tetrachlorocuprate Li$_2$CuCl$_4$ or copper (I) iodide, which is used in an amount of 10 to 40 milli moles per mole of the Grignard reagent. It is preferable in respect of the yield of the reaction product to add the unsaturated-hydrocarbyl acetate dropwise to the Grignard mixture rather than to add the Grignard mixture to the acetate. The amount of the acetate compound is in the range from 0.5 to 1.2 moles or, preferably, from 0.6 to 0.8 mole per mole of the Grignard reagent and the reaction is carried out at 10° to 30° C.

After completion of the Grignard coupling reaction, the reaction mixture is admixed with an aqueous solution containing, for example, 5% of ammonium chloride and 5% of hydrogen chloride at a temperature of 40° C. or below to effect the hydrolysis of the reaction product by the coupling reaction to give the desired unsaturated alcohol compound as the final product.

It is also a possible way instead of the hydrolysis that the reaction product of the Grignard coupling reaction is further reacted with another reactant to introduce a functional group of a different type. For example, acetic anhydride or propionic anhydride is added dropwise to the reaction mixture at 60° to 70° C. to give the corresponding acetate or propionate. Dropwise addition of an acid chloride such as propionyl chloride or acetyl chloride to the reaction mixture at 10° to 30° C. also gives the propionate or acetate. A silyl ether can be obtained by the dropwise addition of a chlorosilane compound such as trimethyl chlorosilane to the reaction mixture. It is of course that each of the above mentioned reactions must be performed under an inert atmosphere of nitrogen, argon and the like.

The final product of the desired unsaturated alcohol can be prepared by subjecting the reaction mixture to a conventional isolation and purification procedure such as distillation, column chromatography, recrystallization, preparative thin-layer chromatography and the like depending on the nature of the product compound. The unsaturated alcohol obtained as the product of the inventive method has a geometrical purity of at least 90% when it is an E-isomer and at least 85% when it is a Z-isomer.

In the following, examples are given to illustrate the inventive method in more detail but not to limit the scope of the invention in any way.

EXAMPLE 1.

(E,E)8,10-Dodecadien-1-ol was synthesized in the following manner.

Into a reaction vessel were introduced 41 g of 6-chlorohexyl alcohol and 100 g of tetrahydrofuran and a Grignard mixture containing 0.3 mole of methyl magnesium chloride in 100 g of tetrahydrofuran was added dropwise to the mixture in the reaction vessel under an atmosphere of nitrogen gas at a temperature of 60° C. or below. After completion of the dropwise addition of the Grignard mixture, the reaction mixture in the vessel was agitated for additional 1 hour at 60° C. to prepare a solution of a magnesium alcoholate. Separately, 7.5 g of metallic magnesium, 100 g of tetrahydrofuran and 1 g of ethyl bromide as a reaction initiator were introduced into another reaction vessel into which the above prepared magnesium alcoholate solution was added dropwise at 70° to 80° C. After completion of the dropwise addition, the reaction mixture in the vessel was further agitated for about 6 hours and then cooled to 20° C. Thereafter, 20 millimoles of dilithium tetrachlorocuprate Li$_2$CuCl$_4$ were added to the mixture and, after several minutes of agitation, a mixture of 30 g of (E,E)-2,4-hexadienyl acetate and 30 g of tetrahydrofuran was added dropwise to the mixture at 20° to 30° C. After completion of the dropwise addition, the mixture was further agitated for several minutes at 30° C. and then 200 g of an aqueous solution containing 5% of ammonium chloride and 5% of hydrogen chloride were added thereto dropwise at 40° C. or below to effect the hydrolysis reaction. The organic solution taken by phase separation of the mixture after the hydrolysis was washed with a 2% aqueous solution of sodium hydroxide and then subjected to distillation to give 32 g of a fraction which was the desired (E,E)-8,10-dodecadien-1-ol having a purity of 92%. The above mentioned yield was 69% of the theoretical value.

EXAMPLE 2.

(E,E)-9,11-Tetradecadien-1-ol was synthesized in the following manner.

Into a reaction vessel were introduced 46 g of 7-chloroheptyl alcohol and 100 g of tetrahydrofuran and a Grignard mixture containing 0.3 mole of ethyl magnesium chloride in 100 g of tetrahydrofuran was added dropwise to the mixture in the reaction vessel under an atmosphere of nitrogen gas at a temperature of 60° C. or below. After completion of the dropwise addition of the Grignard mixture, the reaction mixture in the vessel was agitated for additional 1 hour at 60° C. to prepare a solution of a magnesium alcoholate. Separately, 7.5 g of metallic magnesium, 100 g of tetrahydrofuran and 1 g of ethyl bromide as a reaction initiator were introduced into another reaction vessel into which the above prepared magnesium alcoholate solution was added dropwise at 70° to 80° C. After completion of the dropwise addition, the reaction mixture in the vessel was further agitated for about 6 hours and then cooled to 20° C. Thereafter, 20 millimoles of copper (I) iodide were added to the mixture and, after several minutes of agitation, a mixture of 33 g of (E,E)-2,4-heptadienyl acetate and 30 g of tetrahydrofuran was added dropwise to the mixture at 20° to 30° C. After completion of the dropwise addition, the mixture was further agitated for several minutes at 30° C. and then 200 g of an aqueous solution containing 5% of ammonium chloride and 5% of hydrogen chloride were added thereto dropwise at 40° C. or below to effect the hydrolysis reaction. The organic solution taken by phase separation of the mixture after the hydrolysis was washed with a 2% aqueous solution of sodium hydroxide and then subjected to distillation to give 38 g of a fraction which was the desired (E,E)-9,11-tetradecadien-1-ol having a purity of 91%. The above mentioned yield was 71% of the theoretical value.

EXAMPLE 3.

(Z)-5-Hexadecen-1-ol was synthesized in the following manner.

Into a reaction vessel were introduced 29 g of 3-chloropropyl alcohol and 100 g of tetrahydrofuran and a Grignard mixture containing 0.3 mole of methyl magnesium chloride in 100 g of tetrahydrofuran was added dropwise to the mixture in the reaction vessel under an atmosphere of nitrogen gas at a temperature of 60° C. or below. After completion of the dropwise addition of the Grignard mixture, the reaction mixture in the vessel was agitated for additional 1 hour at 60° C. to prepare a solution of a magnesium alcoholate. Separately, 7.5 g of metallic magnesium, 100 g of tetrahydrofuran and 1 g of ethyl bromide as a reaction initiator were introduced into another reaction vessel into which the above prepared magnesium alcoholate solution was added dropwise at 70° to 80° C. After completion of the dropwise addition, the reaction mixture in the vessel was further agitated for about 4 hours and then cooled to 20° C. Thereafter, 20 millimoles of dilithium tetrachlorocuprate Li$_2$CuCl$_4$ were added to the mixture and, after several minutes of agitation, a mixture of 50.4 g of (Z)-2-tridecenyl acetate and 40 g of tetrahydrofuran was added dropwise to the mixture at 20° to 30° C. After completion of the dropwise addition, the mixture was further agitated for several minutes at 30° C. and then 200 g of an aqueous solution containing 5% of ammonium chloride and 5% of hydrogen chloride were added thereto dropwise at 40° C. or below to effect the hydrolysis reaction. The organic solution taken by phase separation of the mixture after the hydrolysis was washed with a 2% aqueous solution of sodium hydroxide and then subjected to distillation to give 35 g of a fraction which was the desired (Z)-5-hexadecen-1ol having a purity of 87%. The above mentioned yield was 70% of the theoretical value.

EXAMPLE 4.

(E,Z)-7,9-Dodecadienyl acetate was synthesized in the following manner.

Into a reaction vessel were introduced 37 g of 5-chloropentyl alcohol and 100 g of tetrahydrofuran and a Grignard mixture containing 0.3 mole of methyl magnesium chloride in 100 g of tetrahydrofuran was added dropwise to the mixture in the reaction vessel under an atmosphere of nitrogen gas at a temperature of 60° C. or below. After completion of the dropwise addition of the Grignard mixture, the reaction mixture in the vessel was agitated for additional 1 hour at 60° C. to prepare a solution of a magnesium alcoholate. Separately, 7.5 g of metallic magnesium, 100 g of tetrahydrofuran and 1 g of ethyl bromide as a reaction initiator were introduced into another reaction vessel into which the above prepared magnesium alcoholate solution was added dropwise at 70° to 80° C. After completion of the dropwise addition, the reaction mixture in the vessel was further agitated for about 5 hours and then cooled to 20° C. Thereafter, 30 millimoles of dilithium tetrachlorocuprate Li$_2$CuCl$_4$ were added to the mixture and, after several minutes of agitation, a mixture of 33 g of (E,Z)-2,4-heptadienyl acetate and 30 g of tetrahydrofuran was added dropwise to the mixture at 20° to 30° C.

After completion of the dropwise addition, the mixture was further agitated for 30 minutes at 30° C. and then the temperature thereof was increased to 65° C. followed by the dropwise addition of 23 g of acetic anhydride to the mixture kept at 65° to 80° C. After completion of the dropwise addition of acetic anhydride, the mixture was further agitated at 70° C. for additional 1 hour and then 200 g of an aqueous solution containing 5% of ammonium chloride and 5% of hydrogen chloride were added thereto dropwise at 40° C. or below to effect the hydrolysis reaction. The organic solution taken by phase separation of the mixture was dehydrated over anhydrous calcium chloride and then subjected to distillation to give 28.6 g of a fraction which was the desired (E,Z)-7,9-dodecadienyl acetate having a purity of 92%. The above mentioned yield was 56% of the theoretical value.

WHAT IS CLAIMED IS:

1. A method for the preparation of an unsaturated alcohol represented by the general formula R—CH=CH(CH$_2$)$_{n+1}$OH, in which R is a hydrogen atom or a monovalent hydrocarbon group having 1 to 10 carbon atoms and the subscript n is an integer in the range from 3 to 10, which comprises the steps of:
(a) subjecting an acetate of an unsaturated alcohol represented by the general formula

R—CH=CHCH$_2$OCOCH$_3$, in which R has the same meaning as defined above, to a coupling reaction with a Grignard reagent represented by the general formula X$^1$Mg(CH$_2$)$_n$OMgX$^2$, in which X$^1$ and X$^2$ are each a halogen atom and n has the same meaning as defined above; and
(b) hydrolyzing the thus obtained product of the coupling reaction.

2. The method as claimed in claim 1 wherein the monovalent hydrocarbon group denoted by R is a group selected from the class consisting of alkyl groups, alkenyl groups, alkynyl groups and aryl groups.

3. The method as claimed in claim 1 wherein the coupling reaction in step (a) is performed in the presence of a copper compound as a catalyst.

4. The method as claimed in claim 3 wherein the copper compound is dilithium tetrachlorocuprate or copper (I) iodide.

5. The method as claimed in claim 3 wherein the amount of the copper compound is in the range from 10 to 40 millimoles per mole of the Grignard reagent.

6. The method as claimed in claim 1 wherein the amount of the acetate of an unsaturated alcohol in step (a) is in the range from 0.5 to 1.2 moles per mole of the Grignard reagent.

7. The method as claimed in claim 1 wherein the coupling reaction in step (a) is performed at a temperature in the range from 10° to 30° C.

8. A method for the preparation of an acetate of an unsaturated alcohol represented by the general formula R—CH=CH(CH$_2$)$_{n+1}$O—CO—CH$_3$, in which R is a hydrogen atom or a monovalent hydrocarbon group having 1 to 10 carbon atoms and the subscript n is an integer in the range from 3 to 10, which comprises the steps of:
(a) subjecting an acetate of an unsaturated alcohol represented by the general formula

R—CH=CHCH$_2$OCOCH$_3$, in which R has the same meaning as defined above, to a coupling reaction with a Grignard reagent represented by the general formula X$^1$Mg(CH$_2$)$_n$OMgX$^2$, in which X$^1$ and X$^2$ are each a halogen atom and n has the same meaning as defined above; and
(b) reacting the thus obtained product of the coupling reaction with acetic anhydride.

* * * * *